United States Patent
Gerrans et al.

(10) Patent No.: US 9,238,126 B2
(45) Date of Patent: Jan. 19, 2016

(54) BIOFEEDBACK CONTROLLED DEFORMATION OF SINUS OSTIA

(75) Inventors: Lawrence J. Gerrans, San Anselmo, CA (US); Erhan H. Gunday, Great Neck, NY (US)

(73) Assignee: SANOVAS INC., Sausalito, CA (US)

(*) Notice: Subject to any disclaimer, the term of this patent is extended or adjusted under 35 U.S.C. 154(b) by 0 days.

(21) Appl. No.: 13/439,534

(22) Filed: Apr. 4, 2012

(65) Prior Publication Data

US 2012/0259217 A1 Oct. 11, 2012

Related U.S. Application Data

(60) Provisional application No. 61/473,448, filed on Apr. 8, 2011.

(51) Int. Cl.
| | |
|---|---|
| *A61M 29/02* | (2006.01) |
| *A61B 17/24* | (2006.01) |
| *A61M 25/10* | (2013.01) |
| *A61B 6/12* | (2006.01) |
| *A61B 6/00* | (2006.01) |

(52) U.S. Cl.
CPC .............. *A61M 29/02* (2013.01); *A61B 17/24* (2013.01); *A61M 25/1018* (2013.01); *A61B 6/12* (2013.01); *A61B 6/501* (2013.01); *A61M 25/1011* (2013.01); *A61M 2025/109* (2013.01); *A61M 2025/1052* (2013.01); *A61M 2025/1086* (2013.01)

(58) Field of Classification Search
USPC ................................... 600/116, 204; 606/199
See application file for complete search history.

(56) References Cited

U.S. PATENT DOCUMENTS

| | | | |
|---|---|---|---|
| 5,275,169 A | 1/1994 | Afromowitz et al. | |
| 5,707,352 A | 1/1998 | Sekins et al. | |
| 7,361,168 B2 | 4/2008 | Makower et al. | |
| 7,462,175 B2 | 12/2008 | Chang et al. | |
| 7,500,971 B2 | 3/2009 | Chang et al. | |
| 7,654,997 B2 | 2/2010 | Makower et al. | |
| 7,727,226 B2 | 6/2010 | Chang et al. | |
| 7,854,744 B2 | 12/2010 | Becker | |
| 2003/0105483 A1* | 6/2003 | Hudson et al. | 606/196 |
| 2003/0130730 A1* | 7/2003 | Cohn et al. | 623/2.36 |
| 2005/0240147 A1* | 10/2005 | Makower et al. | 604/96.01 |
| 2009/0312745 A1* | 12/2009 | Goldfarb et al. | 604/514 |
| 2010/0010470 A1* | 1/2010 | Bates | 604/509 |

(Continued)

OTHER PUBLICATIONS

Kuhn, F., et al.; "Balloon catheter sinusotomy: One-year follow-up-Outcomes and role in functional endoscopic sinus surgery" Otolaryngol Head Neck Surg 2008; 139: S27-S37.

(Continued)

*Primary Examiner* — Long V Le
*Assistant Examiner* — Ellsworth Weatherby
(74) *Attorney, Agent, or Firm* — St Onge Steward Johnson and Reens LLC

(57) ABSTRACT

A method of dilating a paranasal sinus ostium of a patient, which includes inserting a catheter having at least one balloon into a sinus ostium having an ostial wall, inflating the balloon by supplying fluid thereto such that the balloon exerts a force on the ostial wall, determining at least one parameter of the balloon, establishing an amount the balloon can be inflated without fracturing the sinus ostium based at least in part on the determined parameter of the balloon, and dilating the sinus ostium by inflating the balloon to an amount that does not exceed the established amount.

32 Claims, 11 Drawing Sheets

(56) References Cited

U.S. PATENT DOCUMENTS

| | | | |
|---|---|---|---|
| 2010/0113939 A1* | 5/2010 | Mashimo et al. | 600/470 |
| 2010/0121270 A1 | 5/2010 | Gunday et al. | |
| 2010/0211007 A1* | 8/2010 | Lesch et al. | 604/97.02 |
| 2010/0286467 A1* | 11/2010 | Pesach et al. | 600/9 |
| 2010/0298862 A1* | 11/2010 | Chang et al. | 606/199 |
| 2011/0004057 A1 | 1/2011 | Goldfarb et al. | |

OTHER PUBLICATIONS

Weiss, R., et al.; "Long-term outcome analysis of balloon catheter sinusotomy: Two-year follow-up" Otolaryngol Head Neck Surg 2008; 139: S38-S46.

Bolger, W., et al.; "Safety and outcomes of balloon catheter sinusotomy: A multicenter 24-week analysis in 115 patients" Otolaryngol Head Neck Surg 2007; 137: 10-20.

* cited by examiner

BIOFEEDBACK CONTROLLED DEFORMATION OF SINUS OSTIA

CROSS-REFERENCE TO RELATED APPLICATIONS

The present application claims the benefit under 35 U.S.C. §119(e) of the U.S. Provisional Patent Application Ser. No. 61/473,448 filed on Apr. 8, 2011, the content of which is incorporated by reference herein in its entirety.

FIELD OF THE INVENTION

The present invention relates to balloon catheters and methods of using such catheters for treating conditions of the nose, nasal cavities and paranasal sinuses. More specifically, the present invention relates to methods utilizing balloon catheters for dilating the sinus ostia, resecting biological material and delivering therapeutic and/or diagnostic agents within the nose, nasal cavities and paranasal sinuses.

BACKGROUND OF THE INVENTION

The removal of unwanted and/or life threatening biological material from interior portions of bodily cavities, such as organs, vessels, articular joints and structures, sinuses, and various bodily lumens, is a very common procedure in various medical specialties and disciplines, such as pulmonology, cardiology, urology, gynecology, gastro-enterology, neurology, otolaryngology, orthopedics, and general surgery. Recently, balloon catheters have been employed to release sinus congestion. Accordingly, various instruments and methods have been employed to perform these procedures, which are generally well known in the art.

The nasal cavity (or nasal fossa) is a large air filled space above and behind the nose in the middle of the face. The floor of the nasal cavity, which forms the roof of the mouth, is made up by the bones of the hard palate: the horizontal plate of the palatine bone posteriorly and the palatine process of the maxilla anteriorly. To the front of the nasal cavity is the nose, while the back blends, via the choanae, into the nasopharynx.

The paranasal sinuses are hollow cavities in the skull connected by small openings, known as ostia, to the nasal canal. Each ostium between a paranasal sinus and the nasal cavity is formed by bone covered by a layer of mucosal tissue. Normally, air passes into and out of the paranasal sinuses through the ostia and into the nasal canal.

The paranasal sinuses include the maxillary sinuses, the frontal sinuses, the ethmoid sinuses, and the sphenoid sinuses. The maxillary sinuses are also called the maxillary antra and are the largest of the paranasal sinuses. They are located under the eyes, in the maxillary bones. The frontal sinuses are superior to the eyes, in the frontal bone, which forms the hard part of the forehead. The ethmoid sinuses are formed from several discrete air cells within the ethmoid bone between the nose and the eyes. The sphenoid sinuses are in the sphenoid bone at the center of the skull base under the pituitary gland. Sinusitis is an inflammation of the sinus lining commonly caused by bacterial, viral and/or microbial infections; as well as, structural issues such as ostial blockage. Symptoms include nasal congestion, facial discomfort, nasal discharge, headache, and fatigue. Sinusitis can be considered acute (last 4 weeks or less) or chronic (12 weeks or longer).

Sinusitis affects 29.3 million people each year, making it one of the most common health problems in the U.S. according to the U.S. Department of Health and Human Services, Centers for Disease Control and Prevention National Center for Health Statistics, Summary Health Statistics for U.S. Adults: National Health Interview Survey, 2009 (2010). It is responsible for great healthcare expenditures and a significant loss of workplace activity.

Another common ailment affecting the nose and paranasal sinuses is nasal polyps. Nasal polyps are benign masses that grow from the lining of the nose or paranasal sinuses. Nasal polyps often result from chronic allergic rhinitis or other chronic inflammation of the nasal mucosa. Nasal polyps are also common in children who suffer from cystic fibrosis. In cases where nasal polyps develop to a point where they can obstruct normal drainage from the paranasal sinuses, they can cause sinusitis.

Various drugs have been used to treat sinusitis, including antibiotics and corticosteroid sprays. However, with the use of intranasal sprays, most of the spray does not actually enter the affected sinuses. Accordingly, introduction of drugs directly into the sinuses has been proposed. For instance, U.S. Pat. No. 7,361,168 to Makower et al. discloses implantable devices that may be positioned within a naturally occurring or man-made cavity or passageway in a nostril, nasal cavity, sinus, etc. via balloon catheters.

Functional Endoscopic Sinus Surgery (FESS) is the most common surgical procedure for clearing blocked sinuses. However, the procedure involves removing bone and tissue, which can lead to post-operative pain, scarring and bleeding. The use of balloon catheters in sinus surgery can minimize or eliminate many of these drawbacks.

One method involves creating a new opening from a sinus into the nose to dilate a sinus ostium or duct, or to excise a sinus. U.S. Pat. No. 7,854,744 to Becker discloses methods of performing balloon catheter astronomy of the maxillary ostium, middle meatal maxillary ostium, and inferior meatal ostium and a method of performing ethmoidectomy of the anterior ethmoid sinus, posterior ethmoid sinus, and sinusotomy of the frontal sinus. The methods generally involve pushing a balloon catheter through the ostia into the desired sinus cavity, inflating the balloon to 9 bar for 20 seconds, and deflating the balloon. This may be repeated. After final deflation, the catheter is removed from the enlarged ostium. The catheters employed by Becker utilize stainless steel catheters with radia of 0.13 inches, length of 4 to 10 inches, and wall thickness of at least 0.035 inches. The catheter tip contains a curved distal tip with an angle of 70° to 180°. The distal tip contains a balloon formed of polyethylene terephthalate with a length of 4 mm to 30 mm and working inflated diameter of 2 mm to 15 mm. The balloon has a distal neck and distal tapered region that is adhered to the distal tip of the catheter using an adhesive, such as cyanoacrylate.

In at least some procedures wherein it is desired to position a balloon catheter in the ostium of a paranasal sinus, it is necessary to advance the balloon catheter through complicated or tortuous anatomy in order to properly position the balloon catheter within the desired sinus ostium. Also, there is a degree of individual variation in the intranasal and paranasal anatomy of human beings, thus making it difficult to use the stiff-shaft preshaped balloon catheters of Becker for use in all individuals. The Becker patent describes the necessity of having available a set of balloon catheters, each having a particular fixed angle so that the physician can select the appropriate catheter for the patient's anatomy.

Accordingly, a series U.S. Patents to Chang et al. (e.g. U.S. Pat. No. 7,727,226) disclose methods utilizing flexible balloon catheter devices for use in ENT procedures. Exemplary methods for improving drainage from a paranasal sinus that has a natural ostium comprise inserting a guidewire to a position near the ostium, using the guide to advance a balloon catheter within the ostium and using the balloon to dilate the natural ostium. A sizing balloon situated around the dilating balloon may be inflated using an imageable inflating medium, such as saline with radioopaque contrast agent or carbon dioxide gas. The distal region of the sizing balloon is imaged to enable the operator to estimate the size of the anatomical opening or the diameter of the narrowest region in a tubular anatomical region. Chang et al. also provide methods for treating mucocysts or other flowable substance containing structures located in the sinus by penetrating the structure, compressing the structure with, for example, the balloon of a balloon catheter to force the contents out of the opening formed by the penetrator, advancing the penetrator into the sinus and opening in the cyst, and positioning the balloon in the sinus using the balloon to force the contents out of the opening formed by the penetrator.

A common risk, however, with the above described methods and apparatus is the possibility of under or over-inflation of the balloon portion of the catheter. In the case of under-inflation, the effect of the catheterization on the ostium may be insufficient and therefore require additional treatments, adding to procedure times and increasing the risk of complications. In the case of over-inflation, the balloon catheter can fracture the ostium, leading to restenosis.

Imaging modalities, such as those used with a sizing balloon, cannot assess information regarding pressure or volume of inflated balloons. Variation in constriction responses associated with the nature of an obstruction highlight the importance of control over dilation set-points such as the rate of dilation, pressure, volume and the diameter of the inflated balloon. Many patient maladies are simply not remedied by these procedures because the methods are not efficient, safe, and reproducible, and/or the instruments employed lack the appropriate physiological measurement and/or feedback necessary to ensure the safety, efficacy, and reproducibility of the procedure.

Further, simple pressure control means, such as those described in US 2003/0105483 to Hudson et al., are not optimal because they only involve controlling pressure to a pre-set level through valve caps. The pre-set can prevent extreme over-inflation, but requires the user to approximate a pre-set value and does not allow for real time monitoring and feedback as the balloon is within a nasal or paranasal lumen. The pre-set also does not account for under-inflation when the diameter of an ostium is larger than anticipated.

Hence, there is a significant need for systems and methods for deforming the sinus ostia that are capable of accurately and directly determining in vivo the size and optionally the compliance of areas of the nose, nasal cavities, and paranasal sinuses, such as the ostia. Such systems and methods should be relatively simple to accommodate a single-use strategy.

SUMMARY OF THE INVENTION

Accordingly, it is an object of the present invention to provide methods for deforming sinus ostia that allow the ostia to deform without fracture.

It is also an object of the present invention to remove biological matter from the paranasal sinuses using a balloon catheter without fracturing the ostia.

It is a further object of the present invention to deliver diagnostic and/or therapeutic agents to the paranasal sinuses without fracturing the ostia.

In order to overcome the deficiencies of the prior art and to achieve at least some of the objects and advantages listed, the invention comprises a method of dilating a paranasal sinus ostium of a patient. The method includes inserting a catheter having at least one balloon into a sinus ostium having an ostial wall; inflating the balloon by supplying fluid thereto such that the balloon exerts a force on the ostial wall; determining at least one parameter of the balloon; establishing an amount the balloon can be inflated without fracturing the sinus ostium based at least in part on the determined parameter of the balloon; and dilating the sinus ostium by inflating the balloon to an amount that does not exceed the established amount.

In some embodiments, the at least one parameter is the pressure of the balloon. In other embodiments, the at least one parameter comprises the volume of the balloon. In yet other embodiments, the at least one parameter is the diameter of the balloon.

In certain embodiments, the method further comprises repeating the steps of determining at least one parameter of the balloon, establishing an amount the balloon can be inflated without fracturing the sinus ostium, and dilating the sinus ostium by inflating the balloon.

In certain advantageous embodiments, the step of inflating the balloon comprises supplying fluid to the balloon with a hand or foot actuated pump and the at least one parameter of the balloon is determined by using at least one measurement made by the hand or foot actuated pump. In some of these embodiments, the method further comprises detecting a balloon type for the catheter inserted into the bodily cavity before inflating the balloon, wherein the step of determining at least one parameter of the balloon is based at least partially on the balloon type detected.

In certain advantageous embodiments, the step of inflating the balloon comprises supplying fluid to the balloon with a pneumo-mechanical pump and the at least one parameter of the balloon is determined by using at least one measurement made by the pneumo-mechanical pump. In some of these embodiments, the method further comprises detecting a balloon type for the catheter inserted into the bodily cavity before inflating the balloon, wherein the step of determining at least one parameter of the balloon is based at least partially on the balloon type detected.

In certain advantageous embodiments, the step of inflating the balloon comprises supplying fluid to the balloon with an electro-mechanical pump and the at least one parameter of the balloon is determined by using at least one measurement made by the electro-mechanical pump. In some of these embodiments, the method further comprises detecting a balloon type for the catheter inserted into the bodily cavity before inflating the balloon, wherein the step of determining at least one parameter of the balloon is based at least partially on the balloon type detected.

In certain advantageous embodiments, the step of inflating the balloon comprises supplying fluid to the balloon with an electro-pneumatic pump and the at least one parameter of the balloon is determined by using at least one measurement made by the electro-pneumatic pump. In some of these embodiments, the method further comprises detecting a balloon type for the catheter inserted into the bodily cavity before inflating the balloon, wherein the step of determining at least one parameter of the balloon is based at least partially on the balloon type detected.

In some embodiments, the step of detecting comprises connecting the catheter to a balloon identification plate, and connecting said identification plate to the pump. In certain of these embodiments, the step of detecting further comprises orienting the identification plate with a key. In some of these embodiments, the pump identifies the balloon from the balloon identification plate electro-mechanically. In other of these embodiments, the pump identifies the balloon from the balloon identification plate electro-optically.

In certain embodiments, the pump includes balloon profile data corresponding to the balloon, and a processor that controls the supply of fluid to the balloon based at least partially on the balloon profile data.

In some embodiments, the processor interprets the balloon profile data and displays a multi dimensional image of the ostium based at least partially on the balloon profile data.

In some advantageous embodiments, the pump further includes an imaging system that can translate data from at least one imaging modality disposed in the catheter.

In certain advantageous embodiments, the processor further interprets direct and/or indirect imaging data and the multi-dimensional image of the ostium is based on the direct and/or indirect imaging data.

In some embodiments, the method further comprises advancing a distal end of a guide device to a desired location in the paranasal sinuses before inserting the catheter, wherein the catheter is inserted into the sinus ostium by advancing the catheter over said guide device. In some of these embodiments, the method further comprises removing the guide device from the paranasal cavity before inflating the balloon.

In certain embodiments, the balloon has an outer wall with a resecting surface, and the method further comprises repeatedly deflating and inflating the balloon by supplying fluid to the balloon in pulsed fashion such that the repeated deflation and inflation causes the resecting surface to resect biological material in the sinus ostium. In some of these embodiments, the biological material comprises polyps. In others, the biological material comprises tumors. In yet others, the biological material comprises edematous tissue.

In some embodiments, the method further comprises delivering a therapeutic and/or diagnostic agent to the ostium via a delivery lumen of the catheter. In some of these embodiments, the step of delivering the therapeutic and/or diagnostic agent to the ostium comprises delivering the agent through at least one opening in the catheter in fluid communication with the delivery lumen.

In certain embodiments, the method further comprises repeatedly deflating and inflating the balloon by supplying fluid to the balloon in a pulsed fashion such that the repeated deflation and inflation causes the abrading surface to abrade biological material in the sinus ostium.

In some embodiments, a wall of the at least one balloon has at least one opening in fluid communication with the delivery lumen and the step of delivering the therapeutic and/or diagnostic agent to the biological material comprises delivering the agent through said at least one opening and inflating said at least one balloon until it contacts said biological material.

In certain embodiments, the therapeutic and/or diagnostic agent comprises an antimicrobial agent. In some embodiments, the therapeutic and/or diagnostic agent comprises an anti-inflammatory agent. In other embodiments, the therapeutic and/or diagnostic agent comprises a vasoconstrictor. In yet other embodiments, the therapeutic and/or diagnostic agent comprises a mucolytic agent. In further embodiments, the therapeutic and/or diagnostic agent comprises an antihistamine. In yet further embodiments, the therapeutic and/or diagnostic agent comprises an anti-cholinergic agent. In other embodiments, the therapeutic and/or diagnostic agent comprises a diuretic.

In certain advantageous embodiments, the catheter includes imaging markers.

DETAILED DESCRIPTION OF THE INVENTION

The present invention provides improved methods of dilating a paranasal sinus ostium, removing biological material, and delivering therapeutic and/or diagnostic agents to tissue in the nose, nasal cavity or paranasal sinuses of a patient. The methods comprise inserting a catheter having at least one balloon into a sinus ostium having an ostial wall; inflating the balloon by supplying fluid thereto such that the balloon exerts a force on the ostial wall; determining at least one parameter of the balloon; establishing an amount the balloon can be inflated without fracturing the sinus ostium based at least in part on the determined parameter of the balloon; and dilating the sinus ostium by inflating the balloon to an amount that does not exceed the established amount.

Figure 1A:
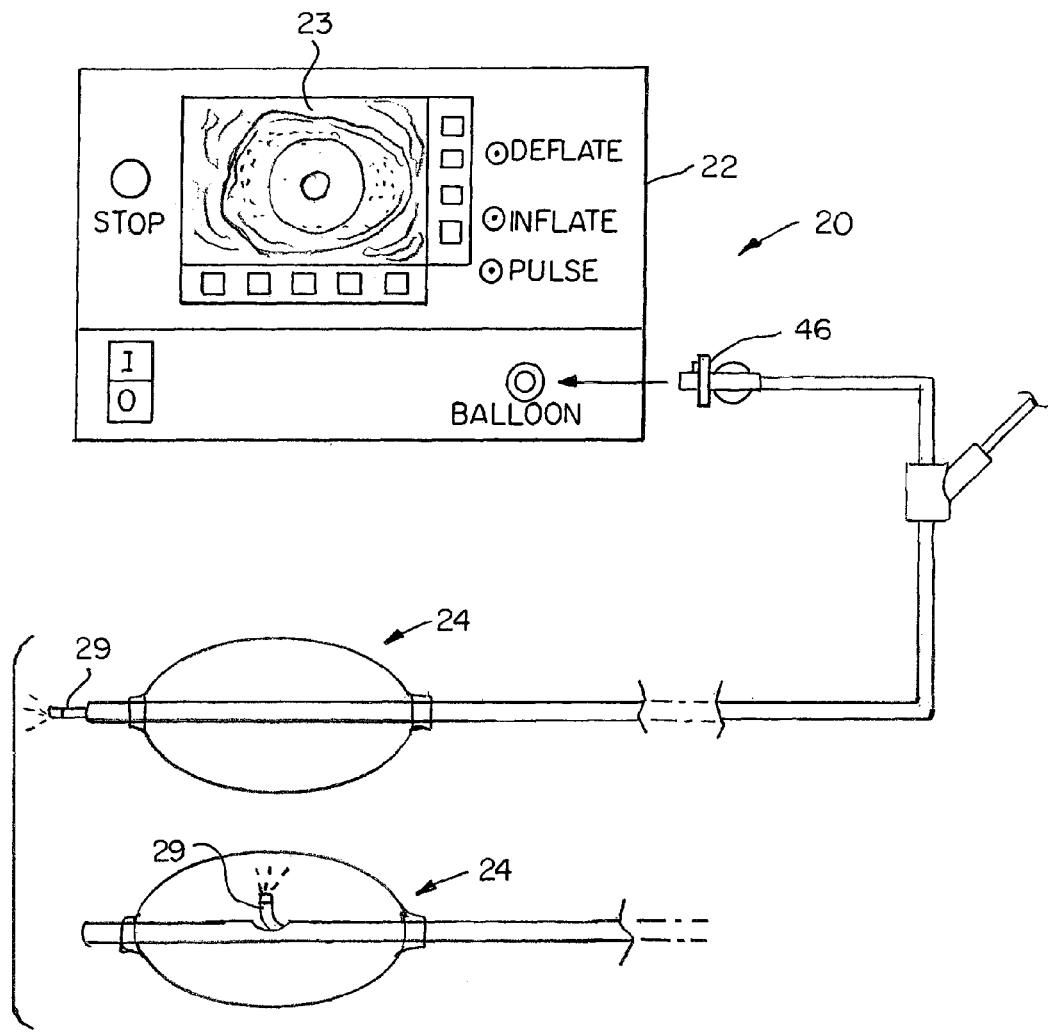
FIGS. 1A-B are front, partially schematic views of a balloon catheter system for use with the methods of the invention.
Figure 1B:
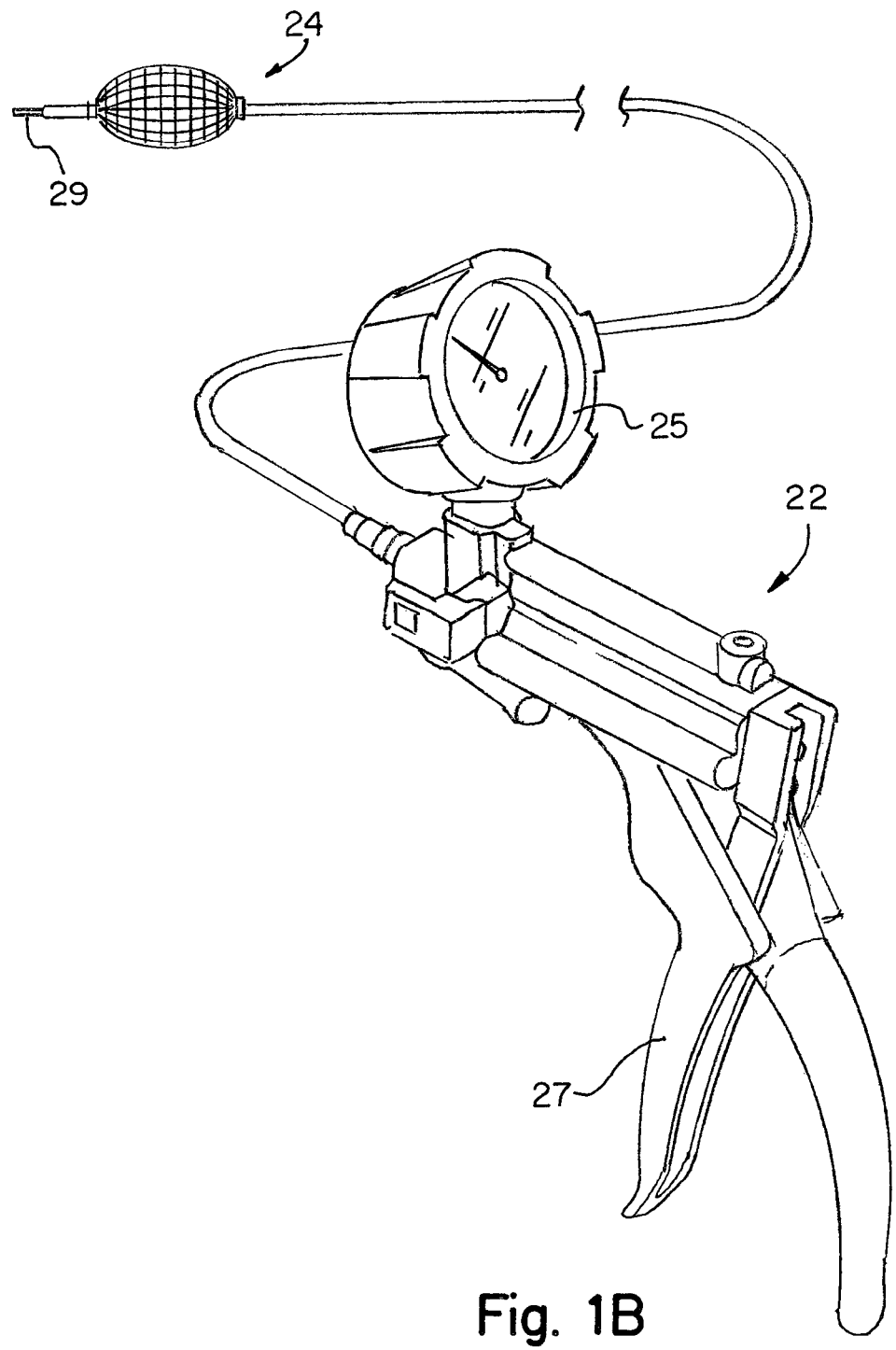

The basic components of a balloon catheter system useful in the methods of the invention are illustrated in FIGS. 1A and 1B. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system (20) includes a fluid source (22), and balloon catheter (24) connected to the fluid source (22), to which the fluid source (22) supplies a fluid, such as a gas, liquid, or mixture thereof. In an advantageous embodiment, the catheter (24) also includes a connection port for insertion of an imaging device (29).

Any suitable fluid source may be used in accordance with the present invention. In the preferred embodiment shown in FIG. 1A, the fluid source is an electro-pneumatic pump having controls on the front thereof, from which a physician or assistant can control the system (as well as a remote control unit). The pump (22) includes a display (23) to facilitate operation by the physician or to display multi-dimensional images of the anatomy in vivo. As shown in FIG. 1B, the fluid source (22) may be a hand or foot actuated pump having an actuator (27) coupled to a gauge (25) for monitoring the flow of the fluid and/or pressure of the fluid delivered to the balloon (30). The fluid may also be provided via a pneumo-mechanical or electro-mechanical pump.

Figure 2:
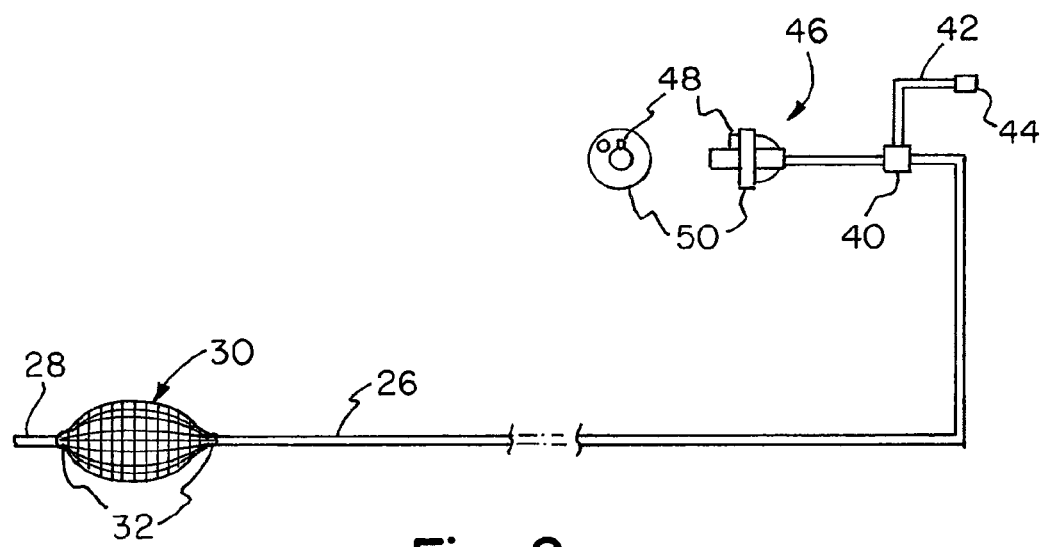
FIG. 2 is a front, partially schematic view of the balloon catheter of the system of FIG. 1A.

As shown in FIG. 2, the balloon catheter (24) includes a catheter (26) made of a polyethylene, or other suitable, material and having an outer diameter of 1 mm to 20 mm, preferably 2 mm to 14 mm, most preferably 3 mm to 7 mm, and a length of about 15 to 40 centimeters. A bendable section (28) having a length of about 3 to 12 mm and an angulation of 5 to 45 degrees at the distal end of the catheter (24) serves as a safety tip. As a result, when the catheter (24) is inserted into a nasal cavity, it will bend instead of puncturing the walls of the cavity.

A balloon portion (30) made of polyurethane, silicone, latex, Yulex, polyethylene, nylon or other suitable material, is located near the distal end of the catheter (24) or at an otherwise desirable, predefined distance along the catheter (24). The balloon (30) comes in a variety of sizes and diameters, which can be selected to suit the particular application for which the device is being used. Typically, such balloons will have lengths of 5 mm to 50 mm, preferably 10 mm to 40 mm, and most preferably 15 to 40 mm. Such balloons will have diameters of 2 to 20 mm, preferably 3.5 mm to 15 mm, and most preferably, 5 to 7 mm. The pump (22) supplies the air at a pressure of approximately 2 atmospheres in order to be able to inflate such balloons to full size, with the particular value depending on the lumen location. By employing relatively low pressures that approximate physiologic conditions, the methods of the present invention have a minimum impact on the physical structure of the nasal cavities. In particular, the structure of any polyp or mucous congestion along the walls of the ostium can be assessed without significant mechanical disruption (as would be the case with methods that determine wall compliance during high pressure).

The balloon (30) may include imaging markers (32), such as radio opaque rings, located at or near the ends thereof. Such markers can be selected and appropriately positioned in order to reflect the relevant waves of various imaging modalities in order to allow the use of such modalities to assist with the precise positioning of the balloon (30).

The balloon may be covered with a flexible resecting surface, which may, for example, comprise a fiber mesh affixed to the surface of the balloon (30). Various textures, such as those described in U.S. Patent Publication No. 2010/0121270 to Gunday et al., the specification of which is incorporated herein by reference in its entirety, may be utilized in the methods of the invention.

Alternatively, the balloon may be covered with surface protrusions to abrade bodily tissues. The abrasion of the bodily tissues perpetuates fluid extravasation processes and stimulates associated cellular absorption of the diagnostic and/or therapeutic agents into the adjacent tissues. The textured outer surface of the balloon can also act as a gripping surface for attachment to bodily tissues.

FIGS. 3 and 4A-C show protrusions (41) on the surface (43) of balloon (30), which may be formed by a fiber mesh affixed to the surface (43) of the balloon (30) during the molding process, that optimize the abrasion capability of the balloon (30). The fiber mesh may be made of lycra, polyurethane, composite springs, or other appropriate material. In other advantageous embodiments, dimensional surface structures or inflatable sinuses that are encapsulated in the surface substrate (43) of the balloon (30) may be used to produce the surface protrusions (41).

Figure 4A:
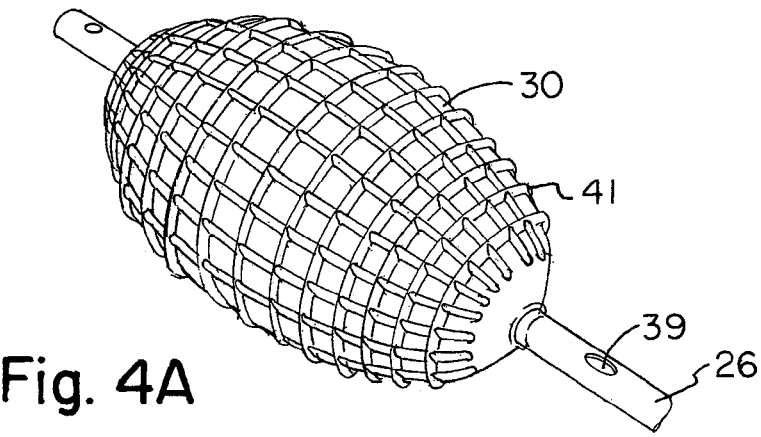
FIGS. 4A-C are enlarged perspective views of an abrading balloon useful in the catheter system of FIGS. 1A-B.
Figure 4B:
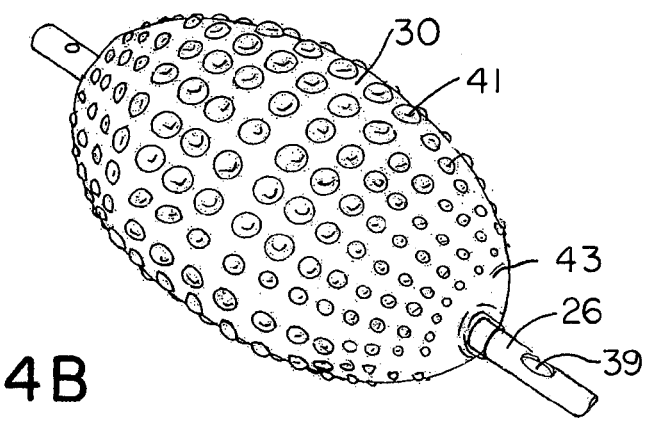
Figure 4C:
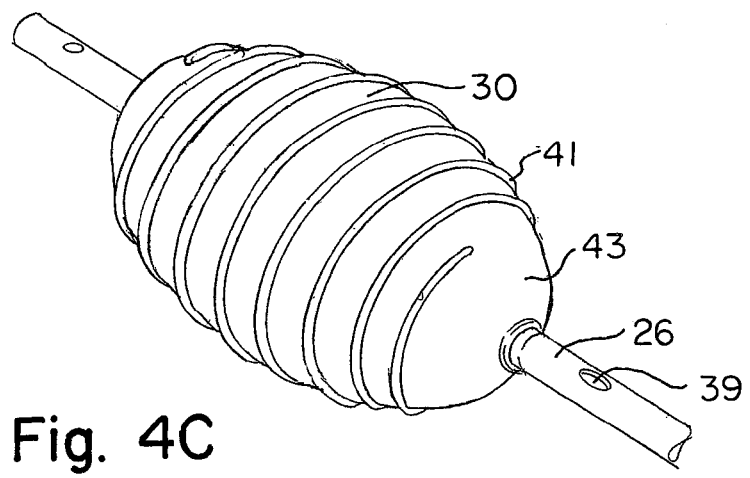

The protrusions (41) forming the abrasive surface of the balloon (30) can have various shapes and configurations, depending on a particular application. For example, as shown in FIG. 4A, the outer surface (43) of the balloon (30) has outwardly extending protrusions (41) that form a lattice-like structure on the surface of the balloon (30). In another advantageous embodiment shown in FIG. 4B, the protrusions (41) are in a form of dimples that extend outwardly from the outer surface (43) of the balloon (32). In yet another advantageous embodiment illustrated in FIG. 4C, the protrusions (41) form a spiral-like pattern that extends circumferentially on the outer surface (43) of the balloon (30). It should be noted that any other shapes and configurations of the surface protrusions can be used in accordance with the present invention.

It is also advantageous, when using an abrading balloon, to include at least one opening (39) in the catheter (26) positioned on either side of the balloon (30). The opening (39) is in fluid communication with a delivery lumen (61) within the catheter (26) to supply a therapeutic and/or diagnostic agent. It should be noted that in some embodiments, the wall of the balloon (30) may have at least one opening therethrough, and the delivery lumen (61) is used to supply the therapeutic and/or diagnostic agent to the chamber (37), which is then delivered to biological material through the openings in the balloons outer surface (43).

Referring back to FIG. 2, the balloon catheter (24) includes an inner lumen breakout Y junction (40) to facilitate the introduction of a guide wire, air bypass, drug delivery, or visualization conduit. The proximal end of the inner lumen (42) after Y junction (40) is terminated with a luer connector (44). The outer lumens are terminated at their proximal end with a keyed connector (46), which includes a key (48) and a balloon identification plate (50).

The Y junction (40) serves several purposes. First, it brings out a separate, inner lumen (42) of the catheter (24) to a suitable connector, such as the aforementioned luer connector (44), in order to provide an independent passage. Additionally, the Y junction (40) also includes a shut-off valve (not shown) for stopping the balloon (30) from deflating. This may be used, for example, when it is required to leave the inflated balloon in place for a lengthy period of time in order to treat chronic bleeding.

As noted above, the catheter (24) is terminated at the proximal end with a keyed balloon identification plate (50). The purpose of this connector is to electronically detect the catheter (24) when it is inserted into the pump (22) and to identify the particular type of balloon catheter being used. The key (48) orients the connector (46) and the identification plate (50) in such a way that the balloon type can be identified by the pump (22) using electro-optical or electro-mechanical means.

Each type of balloon (30) that can be used with the pump (22) is characterized, and balloon profile data is registered in lookup tables. By identifying the type of balloon (30) that is connected the pump (22), the appropriate profile data can be retrieved and used to ensure that the appropriate pressure, volume, flow, and timing adjustments can be made to safely and effectively operate the balloon (30). The balloon profile data contained in the lookup table, along with appropriate pressure and flow measurements (as further discussed below), allows one to make biological material density approximations. This balloon profile data, along with approximated lumen (ostium or sinus) diameter, biological material density, as well as any user commands, are used to adjust the amount of gas the pump (22) delivers to the balloon (30) in order to achieve the desired inflation and deflation amounts.

Figure 3:
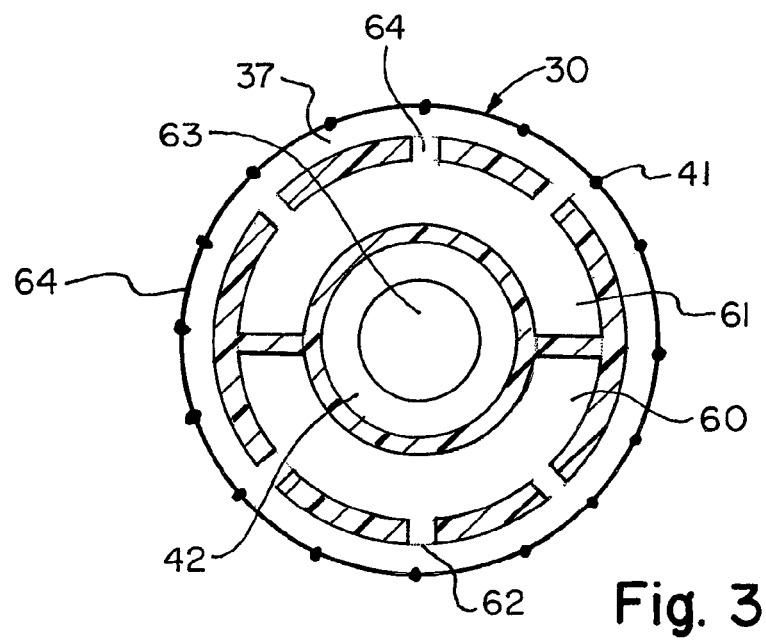
FIG. 3 is a partially cross-sectional view of the deflated balloon of the system of FIG. 2.

Referring to FIG. 3, the inner lumen (42) is used as a means for accurately positioning the balloon catheter (24) as a conduit for a guide wire (63) when inserting the deflated balloon catheter (24) into the bodily cavity. The outer lumen (60) of the catheter (26) is used to inflate and deflate the balloon (30) through the holes (62) provided in the catheter's outer walls (64). The outer lumen (60) is blocked at the distal end of the balloon (30) so that air intended for inflation and deflation will not escape.

In certain advantageous embodiments, delivery lumen (61) and holes (64) are used to deliver, for example, a medicinal drug when used in conjunction with a balloon (30) having abrading protrusions (41). The lumen (61) and holes (64) can be used to deliver any number of things to assist with opening the cavity, circulation, aspiration, respiration, assisting the decomposition of an obstruction, or stimulating healing in the affected area, including air, aspirates, drugs, biologics, biogenetic agents, nano-particulates, solutions, stem cell and gene therapies, and stents and scaffolds. Examples of diagnostic or therapeutic agents are contrast agents, a pharmaceutically acceptable salt or dosage form of an antimicrobial agent (e.g., antibiotic, antiviral, anti-parasitic, antifungal, etc.), an anesthetic agent, an analgesic agent, a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, or immunomodulator), an allergen or another substance that causes secretion of mucous by tissues, anti-proliferative agents, hemostatic agents to stop bleeding, cytotoxic agents (e.g. alcohol), biological agents such as protein molecules, stem cells, genes or gene therapy preparations etc.

Antimicrobial agents can include, but are not limited to, acyclovir, amantadine, amikacin, gentamicin, tobramycin, amoxicillin, amphotericin B, ampicillin, sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clavulanate, clotrimazole, ciprofloxacin, clarithromycin, clindamycin, dapsone, dicloxacillin, doxycycline, erythromycin, fluconazole, foscarnet, ganciclovir, atifloxacin, imipenem, cilastatin, isoniazid, itraconazole, ketoconazole, metronidazole, nafcillin, nystatin, penicillin, penicillin G, pentamidine, piperacillin, rifampin, quinupristin-dalfopristin, ticarcillin, trimethoprim, sulfamethoxazole, tazobactam, valacyclovir, vancomycin, mafenide, silver sulfadiazine, mupirocin, nystatin, triamcinolone, butoconazole, miconazole, tioconazole, and combinations thereof.

Anti-inflammatory agents can include, but are not limited to, beclomethasone, flunisolide, fluticasone proprionate, triamcinolone acetonide, budesonide, loterednol etabonate, mometasone, aclometasone, desonide, hydrocortisone, betamethasone, clocortolone, desoximetasone, fluocinolone, flurandrenolide, prednicarbate, amcinonide, desoximetasone, diflorasone, fluocinolone, fluocinonide, halcinonide, clobetasol, salicylic acid derivatives, aspirin, sodium salicylate, choline magnesium trisalicylate, salsalate, diflunisal, sulfasalazine, olsalazine, acetaminophen, indomethacin, sulindac, tolmetin, dicofenac, ketorolac, ibuprofen, naproxen, flurbiprofen, ketoprofen, fenoprofen, oxaprozin, mefenamic acid, meloxicam, piroxicam, meloxicam, nabumetone, rofecoxib, celecoxib, etodolac, nimesulide and combinations thereof.

Exemplary decongestants include, but are not limited to, pseudoephedrine, xylometazoline, oxymetazoline, phenylephrine, epinephrine, and combinations thereof.

Mucolytic agents can include, but are not limited to, acetylcysteine, guaifenesin and combinations thereof.

Anti-histamines can include, but are not limited to, cromolyn, nedocromil, azelastine, diphenhydramine, loratidine, and combinations thereof.

An exemplary anti-cholinergic is ipratropium bromide.

Diuretics can include, but are not limited to, furosemide and/or hyperosmolar agents such as sodium chloride gel or other salt preparations.

In certain applications, it may be desirable to locally deliver in a similar manner agents that will facilitate photodynamic therapy. Likewise various forms of energy can be delivered locally, including laser, microwave, RF, cryogenic, and thermal energies.

In certain embodiments, the balloon catheter can include a multi-balloon construct at its distal end. This construct may include, for example, a proximal balloon segment, a center balloon segment, and a distal balloon segment as described in U.S. Patent Publication No. 2010/0121270 to Gunday et al., incorporated herein by reference. In this way, with the proximal and distal balloons remaining inflated, the drug is contained in the targeted site and evenly distributed as biological material is resected or abraded.

In a preferred embodiment, the openings (39) are used to accommodate the imaging device (29), which extends out of the opening (39) to view surrounding tissue during the insertion of a multi-balloon catheter into the bodily cavity.

Additionally, in some of the multiple-balloon embodiments, the above-described imaging markers (e.g., radio opaque rings), can be located at or near the ends of each balloon segment in order to facilitate the use of certain imaging modalities to assist with the precise positioning of the balloons.

Figure 5A:
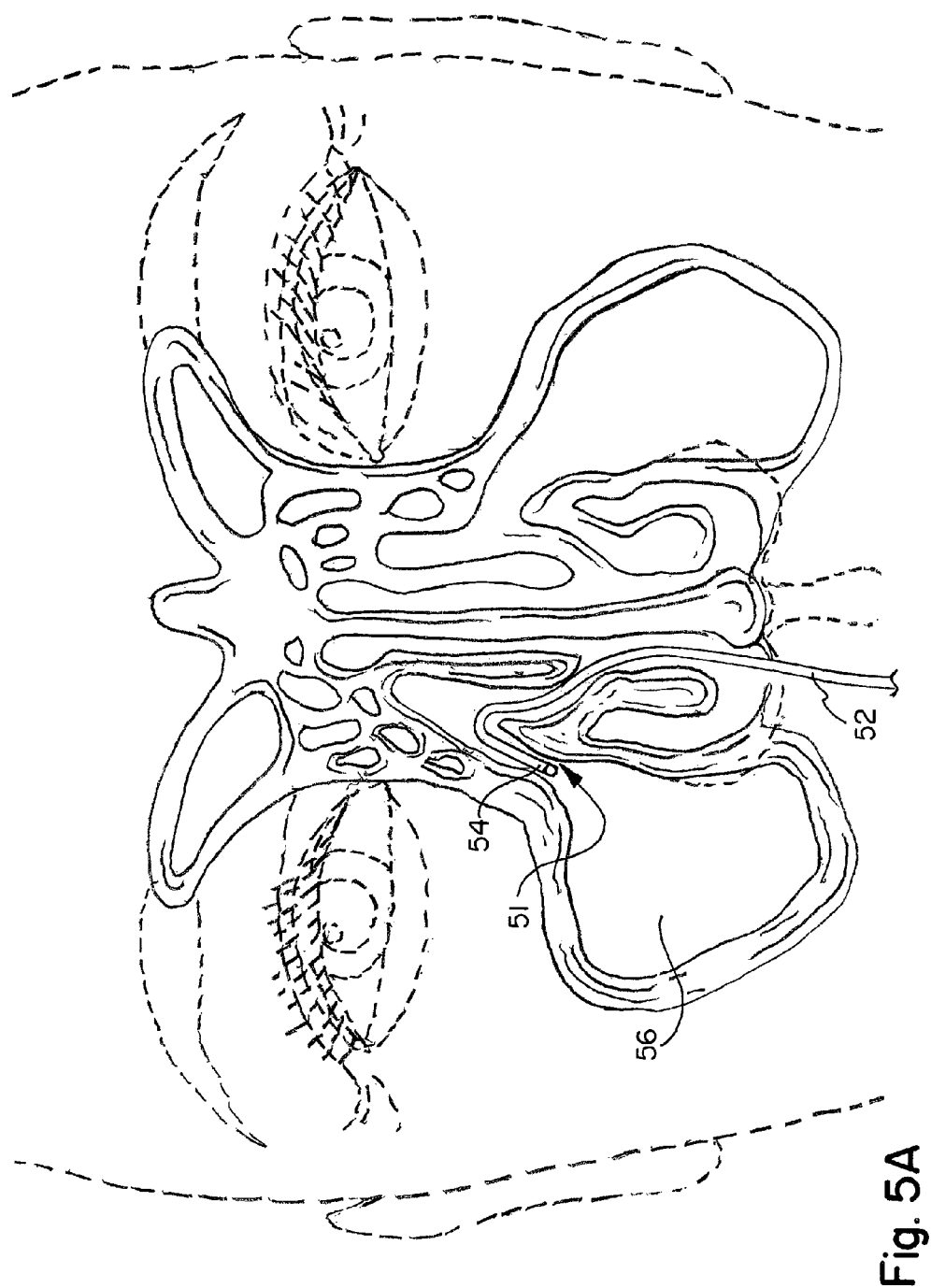
FIG. 5A shows a method of accessing a maxillary sinus ostium using a guide catheter.

A method for operation of the balloon catheter system (20) for dilating ostia can be generally described with reference to FIGS. 5A-H. FIG. 5A shows a method of accessing a maxillary sinus ostium (51) using guide catheter (52). Guide catheter (52) is introduced through a nostril and advanced in the paranasal anatomy such that a safety tip (54) is located inside or adjacent to a maxillary sinus ostium (51). The catheter (52) is flexible and steerable or pre-shaped such that a proximal bent, curved, or angled region allows guide catheter (52) to be positioned around the inferior turbinate and the middle turbinate.

Figure 5B:
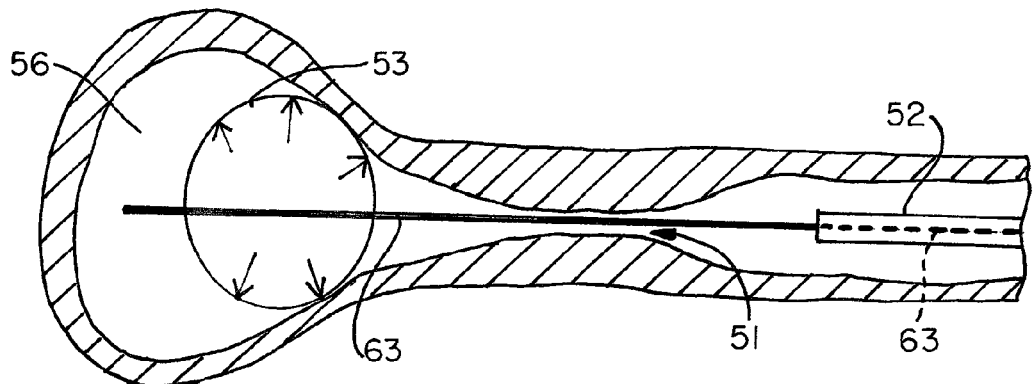
FIGS. 5B-H are side, partially cross-sectional views of the balloon catheter of FIG. 1 being operated in the ostium and maxillary sinus of FIG. 5A.

As shown in FIG. 5B, a guidewire (63) or a suitable diagnostic or therapeutic device may then be introduced through the lumen of guide catheter (52) into the maxillary sinus (56). In some embodiments, the guidewire (63) includes a balloon (53) which is inflated once in the maxillary sinus to anchor the guidewire in place.

Figure 5C:
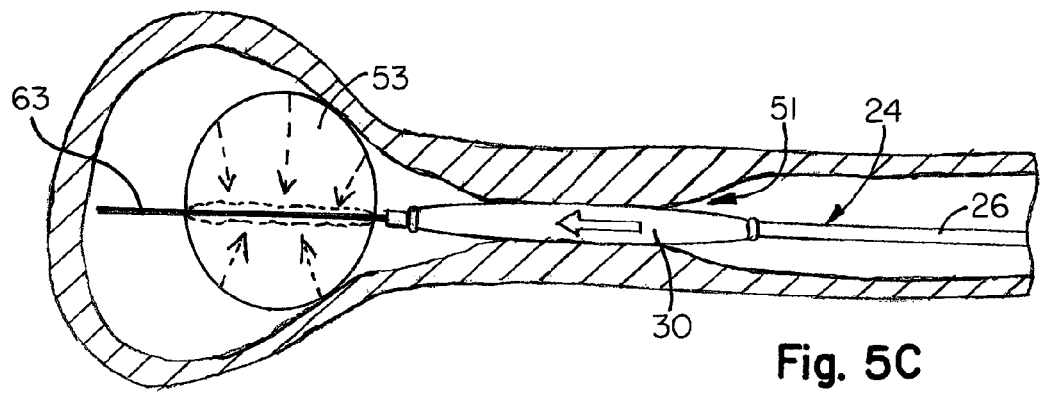

Referring to FIG. 5C, after a visual inspection via an endoscope, CT-scan, x-ray, or other anatomical mapping means, a balloon catheter (24) is selected, and the deflated device is inserted into a nasal passage until the balloon (30) is positioned in the desired ostium. This may be accomplished by inserting the proximal end of the guidewire (63) into a lumen of the catheter (24) and sliding the catheter (24) over the guide wire (63). The balloon (53) is then deflated, and the guidewire (63) is pulled out through the inner lumen of the catheter (24). The balloon catheter (24) is connected to a pump (which is further described in detail below), at which time the pump determines the type of balloon catheter that has been inserted. The pump may render a multi-dimensional image of the anatomy in vivo on the display based on the balloon profile data alone or in concert with direct and/or indirect imaging methods and imaging guidance.

Figure 5D:
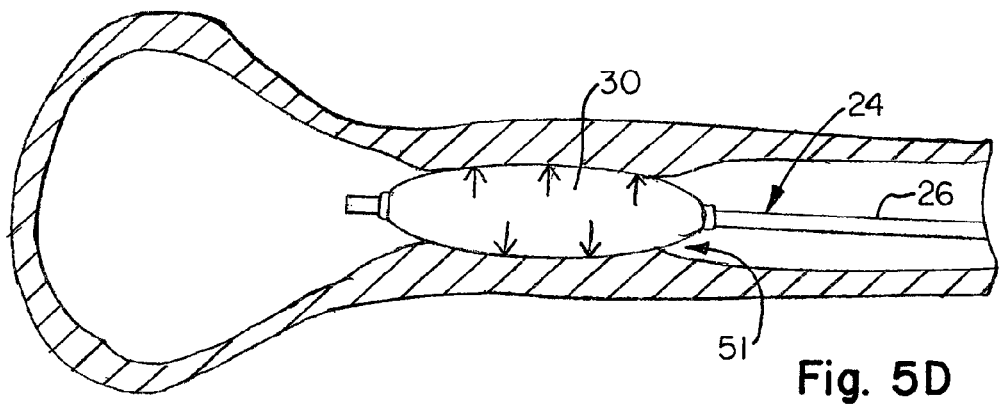

Referring next to FIG. 5D, the balloon (30) is inflated by the pump (which knows the type of balloon to which it is connected) at an air pressure of approximately 2 atmospheres for a fixed amount of time, and the flow is measured (after the physician presses an inflate button on the pump). Each "inflate" command will inflate the balloon by an incremental amount based on the type of balloon that is connected. This incremental inflation is accomplished by opening an inflate valve for a set amount of time while a deflate valve remains closed. In this way, the balloon is inflated to the size desired by the user. Alternatively, pressing and holding the inflate button will inflate the balloon in a continuous fashion.

While inflating, the flow of gas (ml/sec) is measured. After closing the inflate valve, the balloon pressure is measured, and an approximation of the volume V is made based on the ideal gas law (V=nRT/P) and a lookup table, which contains balloon characteristics and universal constants. Here, T is assumed constant at 310° K (body temperature can be measured and entered into the equation as well), R is a gas law constant, n is moles of gas, which is proportional to the measured flow, and P is the measured pressure. With each incremental inflation, V is recalculated, and the relative volume change (V2-V1) is displayed. Knowing the shape of the balloon from the balloon identification, and using the data from the lookup table, the relative change in balloon diameter (D2-D1) is also calculated and displayed. On the basis of information obtained during this step, the balloon catheter (24) may be repositioned, and this repeated, if necessary.

Figure 5E:
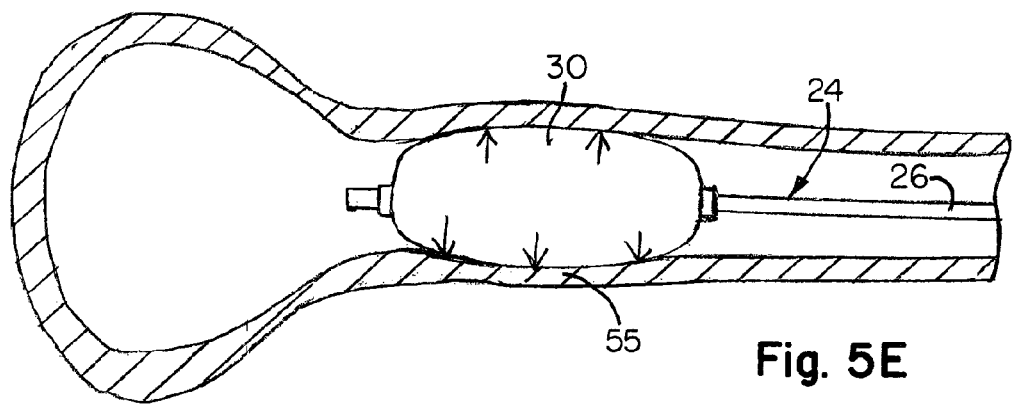
Figure 5F:
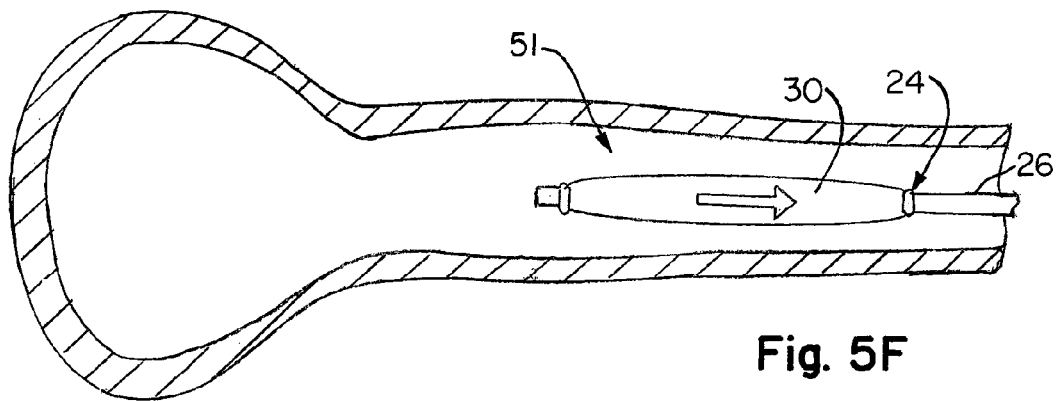
Figure 5G:
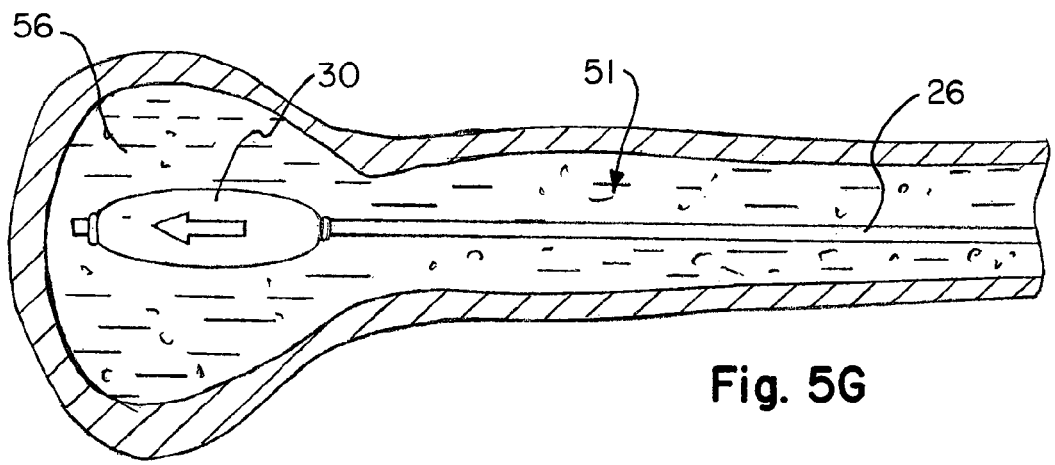
Figure 5H:
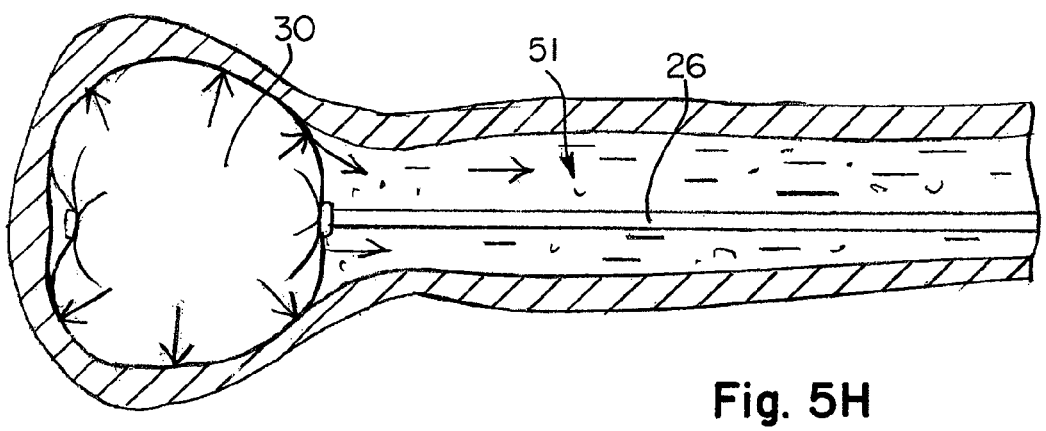

Thereafter, as shown in FIGS. 5E-F, the balloon (30) is further inflated such that it exerts a force on the ostial wall, thereby dilating the ostium (51). As the pump is operated, data from the measurements and calculations is continuously updated and displayed. Based on the determined pressure and/or other parameters noted above and any predetermined threshold values set in the pump (e.g., a maximum balloon pressure), the pump continues to supply the balloon with fluid until it reaches an amount less than that which would cause the sinus ostium to fracture. When the diameter of the ostium (51) has been dilated to the maximum diameter, the balloon is deflated and removed from the lumen (51). As shown in FIG. 5G-H, optionally, it may be desirable to push the deflated catheter into to the sinus (56) beyond the ostium (51), and reinflate balloon (30) to push any fluid out of the sinus through the now widened ostium (51).

A method for operation of the balloon catheter system (20) for delivering a therapeutic and/or diagnostic agent to biological material in the nose, nasal cavity or paranasal sinuses can be generally described with reference to FIGS. 6A-C. Although shown delivering agents to a target biological material (53), the method can also be used for delivering agents into a sinus, i.e. the maxillary sinus.

Figure 6A:
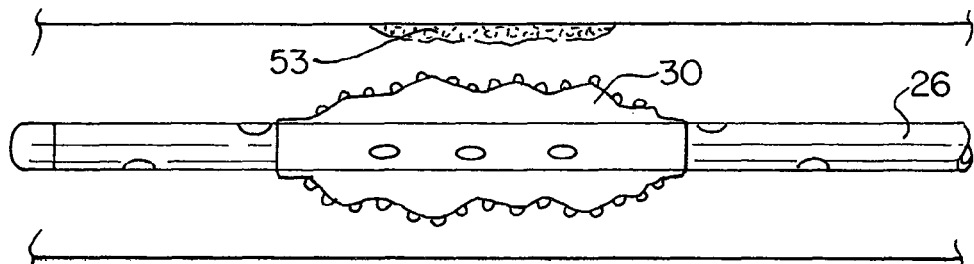
FIGS. 6A-C are partially exposed, isometric views of the catheter system of FIG. 1 being operated in a bodily cavity.
Figure 6B:
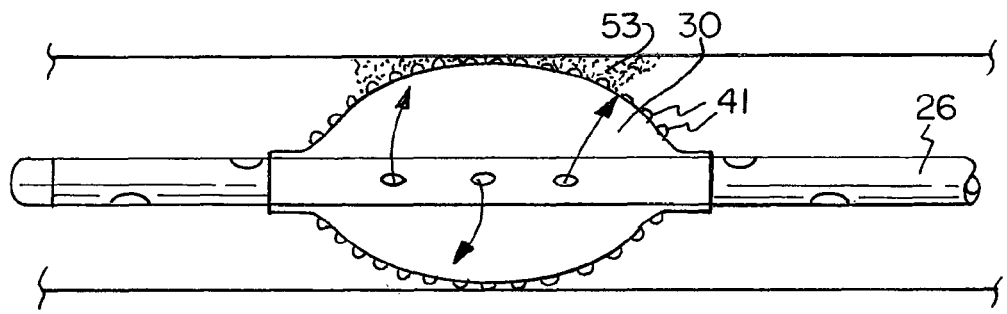

Referring to FIG. 6A, after a visual inspection via an endoscope, CT-scan, x-ray, or other anatomical mapping means, a balloon catheter (24) having abrading protrusions (40) is selected, and the deflated device is inserted into the nasal cavity with the balloon (30) positioned adjacent to the target biological material (53). This may be accomplished by using a guide catheter (52) and a guide wire (63), as previously noted. The balloon catheter (24) is connected to a pump, at which time the pump determines the type of balloon catheter that has been inserted.

As shown in 6B, the balloon (30) is then inflated by the pump as previously described. This causes the abrasive outer surface (41) to contact the biological material (53) and creates surface abrasions in the biological material. The surface abrasions act to create capillary blood flow and to instigate flow of white blood cells to the biological material, which facilitates absorption of an agent into the biological material. The pressure regulator and flow meter along with the known dimensions of the balloon provide feedback to the pump necessary to determine dimensions and resistance of the biological material from which a determination is made as to the diameter of the ostium and the density of the biological material. Using theses parameters, the microcontroller makes the appropriate pressure and timing adjustments necessary to maximize the effectiveness of the balloon, provide the physiologic metrics of the affected and non-affected areas, and provide data points and indicators related to the specific dimensional and density characteristics of the intra-ostial anatomy and pathology and aid the physician in safely determining and delivering treatment.

The balloon (30) can be sequentially pulsed to create further surface abrasions. When a pulse button on the pump is pressed, the balloon (30) is deflated and inflated in a cyclical fashion, based either on parameters that were entered by the user, or on default parameters selected by the pump, which are based on the characteristics of the particular balloon (which has been identified as a result of the aforementioned balloon identification plate) and the diameter and/or density measurements made by the system. In this way, the pulse mode of the pump causes the balloon to pulsate according to a desired frequency or change in volume within the balloon, producing a periodically recurring increase and decrease in balloon size.

Figure 6C:
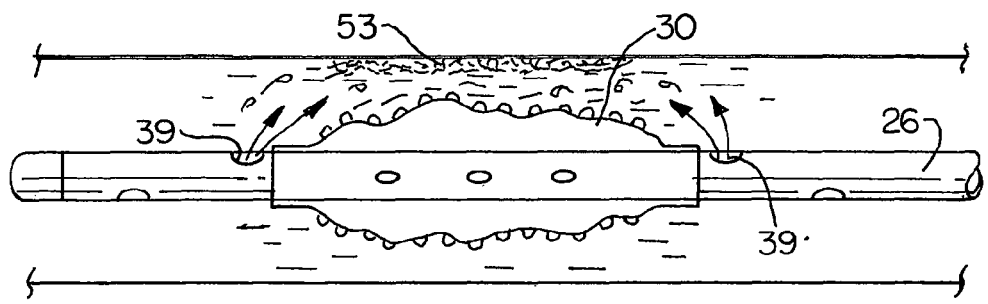

A therapeutic and/or diagnostic agent is then delivered via the openings (39) in the catheter (26), as shown in FIG. 6C. It should be noted that the agent can also be delivered through a plurality of openings provided in balloon (30). As the agent is delivered, it coats the outer surface of the balloon (30). The balloon (30) is inflated, such that the outer surface of the balloon contacts the biological material (53), and is kept that way for a desired period of time. The balloon (30) is then at least partially deflated, recoated with the agent, re-inflated and kept that way again. This sequential and/or constant expansion of the balloon (30) instigates extravasation and initiates fluid extravasation through the vessel walls and into the adjacent biological material.

Figure 6D:
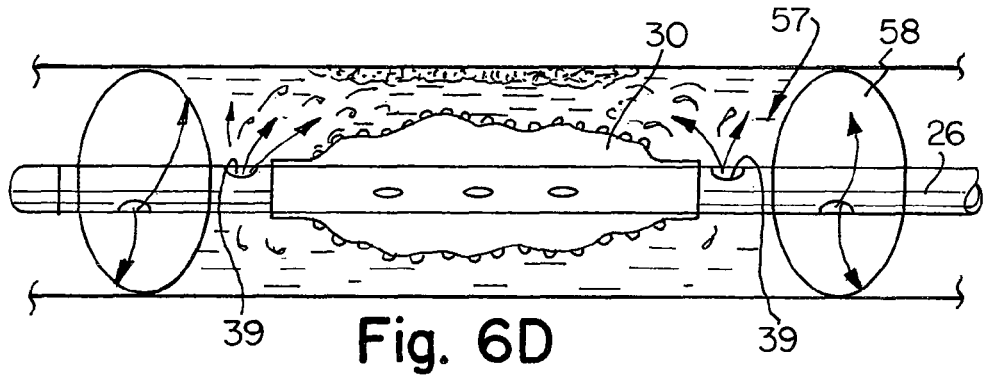
FIG. 6D is a partially exposed, isometric view of the catheter system of FIG. 1 having multiple balloons being operated in a bodily cavity.

In a multi-balloon construct (57), as shown in FIG. 6D, the proximal balloon (58) can be independently inflated to create a drug delivery chamber to contain the agent and aid the volumetric pressure requisite to the extravasation of the agent into the submucosal tissues and sinus.

In an advantageous embodiment, an imaging device disposed in one of the lumens of the catheter (26) is used to help position the balloon at the proper location. Preferably, the imaging device extends out of the opening (39) in the catheter (26), such that the tissue in front of the catheter can be viewed by the imaging device during the insertion of the multi-balloon catheter (57) into a bodily cavity.

Once the agents have been delivered and extravasted into the biological material at the target site, any remaining agent can be evacuated via the same openings (39) and lumens through which they were supplied using suction. In certain advantageous embodiments, the pump provides a negative pressure to vacuum out the agents. The various lumens and corresponding openings (39) can be used to cyclically deliver and evacuate the agents and various other fluids instantly, sequentially, intermittently and/or continuously over designated time intervals.

Figure 7A:
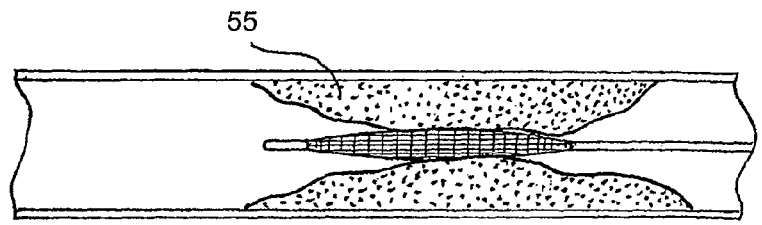
FIGS. 7A-F are side, partially cross-sectional views of the balloon catheter of FIG. 1 being operated in a bodily cavity.

The operation of the balloon catheter system (20) for resecting polyps or other undesirable biological material (55) from the nose, nasal cavity or paranasal sinuses can be generally described with reference to FIGS. 7A-F. Referring first to FIG. 7A, after a visual inspection via an endoscope, CT-scan, x-ray, etc., a balloon catheter is selected, and the deflated device is inserted into position in a bodily cavity. This may be accomplished by using the working channel of an endoscope and guide wire, as previously noted. The catheter is connected to the aforementioned pump.

Figure 7B:
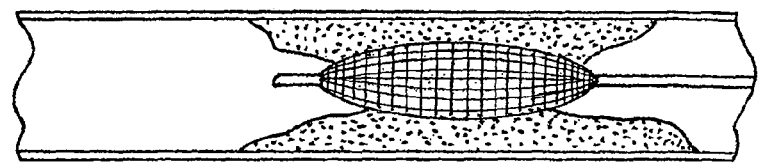
Figure 7C:
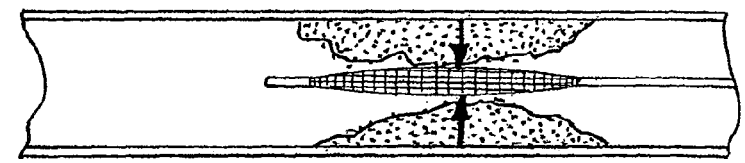
Figure 7D:
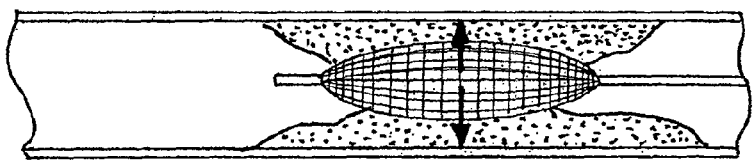

Referring next to FIG. 7B, the balloon is inflated by the pump and the pump calculates the initial approximation of the biological material density and the size of the opening in which it is located, and displays the results for confirmation by the physician. As shown in FIGS. 7C-D, when a pulse button on the pump is pressed, the pump causes the balloon to pulsate according to a desired frequency or change in volume within the balloon, producing a periodically recurring increase and decrease in balloon size.

Accordingly, the resecting surface of the balloon repeatedly comes into contact with the biological material to create micro-impacts thereon. As the balloon is deflated and inflated, the resecting surface creates just enough interference fixation, concentrically, along with compressive force excitation and friction upon the unwanted biological material, to promote compressive force exhaustion and abrasion to elicit the decomposition and excision thereof, such that the targeted biological material is resected in a non-traumatic way. As the biological material is destroyed and removed, the balloon is inflated to a larger starting diameter and these steps are repeated until all the unwanted biological material is resected.

Meanwhile, the pump continually monitors the balloon pressure and gas flow, and it updates a graphical display accordingly. This gives the physician an indication as to when to stop the pulse mode and evacuate the loosened biological material.

Figure 7E:
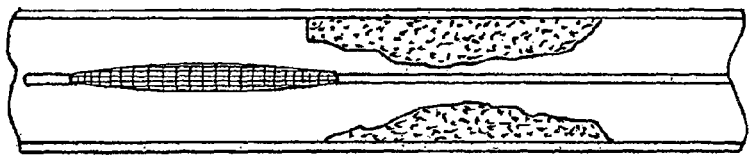

Referring to FIG. 7E, once the obstruction is broken up, the balloon is deflated (by pressing a deflate button on the pump), and the balloon is inserted further distally into the bodily cavity, past the location of unwanted biological material.

Figure 7F:
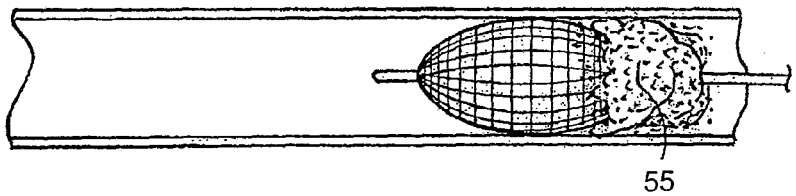

A shown in FIG. 7F, the balloon is then re-inflated (by pressing the inflate button on the pump) and gently pulled towards the proximal end, bringing with it the loose biological material and debris to a point where it can be removed using forceps or suction. In a multi-balloon construct, the debris can be removed through one of the available lumens.

While the resecting and abrading have been described with respect to the pulsation mechanism of action described herein, such action is not exclusive. That is, other mechanisms of action may be employed in addition to pulsation as needed, such as linear translation of the balloon along the catheter, as well as rotation. These motions are particularly useful in mucosa resection.

Figure 8:
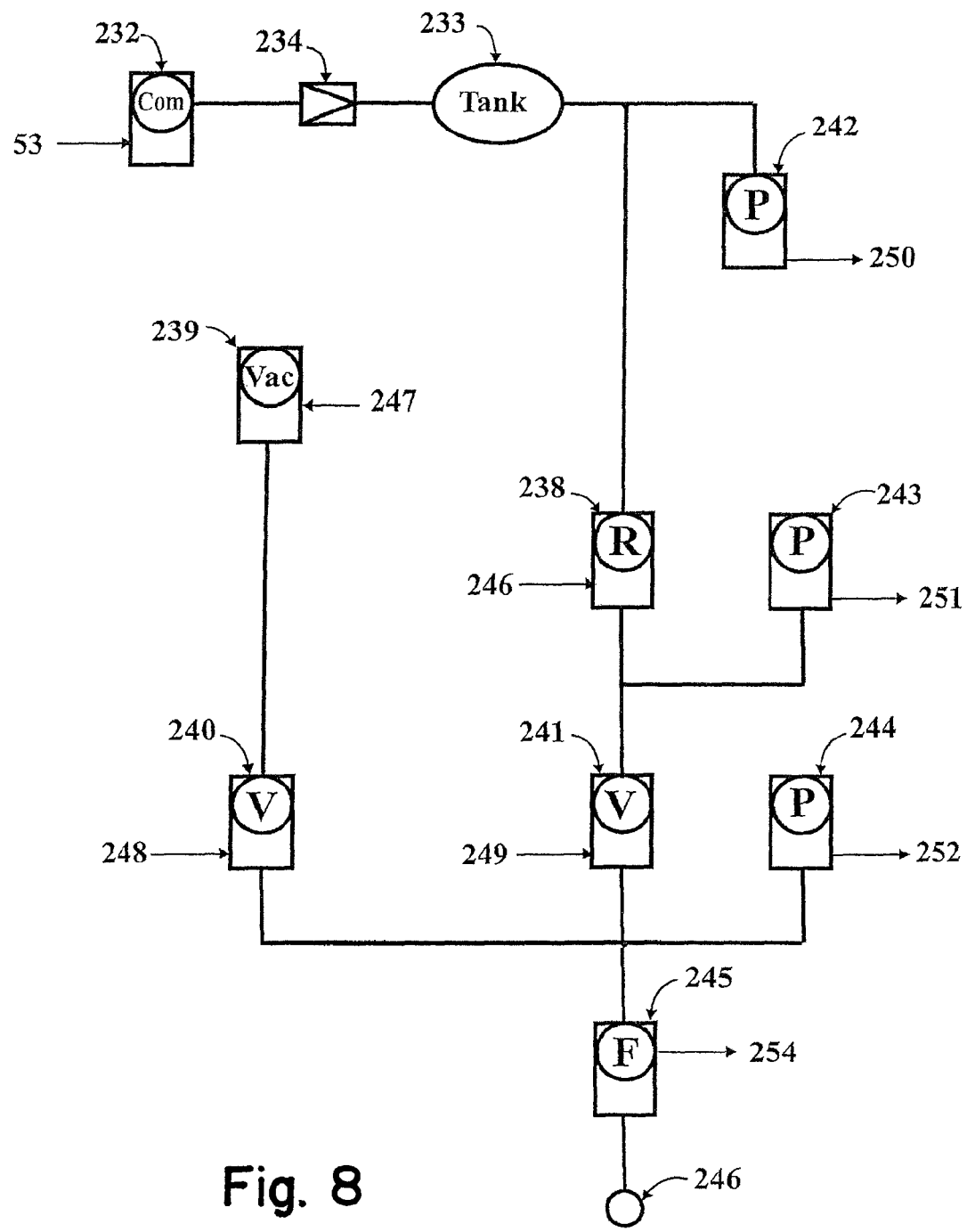
FIG. 8 is a block diagram illustrating the pneumatics of the pump of FIG. 1.

A pump (22) that controls the operation of the balloon (30) described above will hereafter be described. FIG. 8 represents a block diagram of the pneumatic components and operation of the pump. The pump includes an air compressor (232) and a pressure tank (233), such as a Festo model CRVZS-0.1, which enable it to achieve up to 10 atmospheres of continuous pressure. The air pressure in the tank (233) is continuously monitored by a microcontroller (254). The microcontroller initiates the compressor (232) to operate via an electrical signal output (253) when the tank pressure drops below 4-5 atmospheres. The size of the tank (233) is selected such that at least one procedure can be completed without the compressor operating. The microcontroller calculates and displays the amount of air in the tank (233), which indicates to the user whether there is enough air to complete the procedure. A check valve (234), such as a Festo model H-1/8-N1, is located between the compressor (232) and the tank (233) in order to prevent the pressured gas from flowing back into the compressor (232). In another variation of the pump (22), however, the above-referenced compressor and pressure tank are not included, and the pressurized air or carbon dioxide is instead provided from an external source, such as a hand actuated pump, $CO_2$ cartridge, gas tank or the operating room walls commonly found in an operating room.

The pressurized gas from the air tank (233) first goes through a pressure regulator (238), which is electronically controlled via an analog electrical output (0V-10V) signal (246) generated by the microcontroller to supply air to the balloon at an exact pressure, which can be set and changed by the physician. However, any pressures higher than the upper limit for the particular balloon being used will generate a warning signal. As explained above, different balloon catheters may be used depending on the application, which are identifiable via key connectors. Therefore, pressure, volume, and flow characteristics of different types of balloons are contained in lookup tables in order to optimize the operation of the balloons and to ensure their consistent performance.

Accordingly, when the pressure is set higher than the balloon's upper limit, the detection of gas flow will cause the pump to stop and produce the warning, and the physician must then take a specific action to override this condition. Similarly, if there is no balloon pressure, the detection of gas flow will also generate a warning, as this may mean the balloon has ruptured. It should further be noted that the pump will also not operate if a catheter is not connected. Additionally, a balloon's operation when first removed from the packaging may vary from its normal operation, requiring that they are first exercised before use in the body. Therefore, the setup and preparation function of the pump allows for this variance.

In certain advantageous embodiments, a vacuum source (239), such as a Festo model VN-05-L-T3-PQ2-VQ2-R01-B, is also included in the pump so that the balloon can be rapidly deflated in a consistent manner. This component also aids in achieving higher frequencies during the pulse mode of operation. The vacuum source (239) is turned on and off by the microcontroller via an electrical output signal (247).

Two microprocessor-controlled solenoid valves—a deflation valve (240) and an inflation valve (241)—are used to control the inflation and deflation of the balloon. The appropriate balloon inflation size is achieved by keeping the gas pressure constant, using the balloon pressure, flow, and volume characteristics from the lookup table data, and timing the on/off activation periods of the valves (240, 241). Deflation valve (240) and inflation valve (241) are controlled by a deflate electrical signal (248) and an inflate electrical signal (249), respectively, which are generated by the aforementioned microcontroller.

The gas pressure is continuously monitored by the microcontroller using pressure regulator (242) at the input from the tank (233), a pressure regulator (243) at the output of the regulator (238), and pressure regulator (244) at the output to the balloon. These pressure regulators, which may be, for example, Festo model SDET-22T-D10-G14-U-M12, provide to the microcontroller analog electrical signal (0V-10V) inputs (250, 251, 252) that vary proportionally to the pressure at the regulators (242, 243, 244). The gas passes through an electronic flow meter (245), such as a Festo model SFET-F010-L-WQ6-B-K1, and a filter (246), before being delivered to the balloon. The flow meter (245) provides an analog electrical signal input (254) to the microcontroller that indicates the amount of gas flow to the balloon.

The pressure regulator (244) and flow meter (245), along with the known dimensions of the balloon, provide the feedback necessary to determine the ostial wall or biological material dimensions and resistance via circumferential force and depth resistance, from which a determination is made as to the ostial diameter or the density of the biological material. Using these parameters, the microcontroller makes the appropriate pressure and timing adjustments necessary to maximize the effectiveness of the balloon, provide the physiologic metrics of the affected and non-affected areas, and provide data points and indicators related to the specific dimensional and density characteristics of the intra-lumen anatomy and pathology to aid the physician in safely determining and delivering treatment.

In this way, the gas pressure is strictly monitored and maintained at 2 atmospheres in order to keep the balloon from bursting. The high gas input pressure (up to 10 atmospheres) is reduced to and regulated at 2 atmospheres electronically and under software control. However, the pressure delivered to the balloon can be increased or decreased under certain conditions via operator commands.

A further explanation of the components and operation of the pump (22) is provided in the aforementioned U.S. Patent Publication No. 2010/0121270 to Gunday et al.

Alternatively, one can use a handheld apparatus to measure the relative level of ostial deformation without fracturing the ostium. For example, one could use a ball pump that remains outside of the body and is connected to the balloon, which includes a pressure gauge. The measurements can be collected by sequential inflation of the balloon using the pump. Alternatively, the device could include transducers at the distal end of the catheter or on balloon, and it may display its measurements as a digital readout. In other cases, an instrument such as a tenaculum could be used to slowly open and control/measure the ostium. The hand actuator can employ a $CO_2$ cartridge in the actuator and be used in conjunction with a mobile device application (e.g., iPhone app), to measure pressure and volume.

Although the above described methods are described with reference to the sinus ostia, the methods of the present invention are suitable for transnasal dilation of other passageways in the ear, nose and/or throat, such as the Eustachian tube and nasolacrimal duct.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of dilating a paranasal sinus ostium of a patient, the method comprising the steps of:
    inserting a catheter having at least one balloon into a sinus ostium of a patient, the sinus ostium having an ostial wall;
    determining the balloon type;
    inflating the balloon by supplying fluid thereto such that the balloon exerts a force on the ostial wall without fracturing the sinus ostium;
    after the balloon is inflated in the sinus ostium, determining a diameter of the inflated balloon;
    while the balloon is inflated in the sinus ostium, calculating a threshold amount to which the balloon can be inflated that will not fracture the sinus ostium of the patient using the determined inflated balloon diameter and setting the threshold amount in a pump having a sensor;
    monitoring the increasing diameter of the balloon while repeatedly deflating and inflating the balloon by supplying fluid to the balloon in a pulsed fashion; and
    using the pump having a sensor to monitor the diameter to determine when to stop inflation of the balloon to an amount that does not exceed the threshold amount.

2. The method of claim 1, wherein the step of inflating the balloon comprises supplying fluid to the balloon and the pump comprises an electro-pneumatic pump and the balloon diameter is determined by using at least one measurement made by the electro-pneumatic pump.

3. The method of claim 1, wherein the step of determining the balloon type comprises connecting the catheter to a balloon identification plate, and connecting said identification plate to the pump, the pump comprising an electro-pneumatic pump that supplies fluid to the balloon during the step of inflating the balloon.

4. The method of claim 3, wherein the step of detecting further comprises orienting the identification plate with a key.

5. The method of claim 3, wherein the pump identifies the balloon from the balloon identification plate electro-mechanically.

6. The method of claim 3, wherein the pump identifies the balloon from the balloon identification plate electro-optically.

7. The method of claim 3, wherein the pump includes balloon profile data corresponding to the balloon, and a processor that controls the supply of fluid to the balloon based at least partially on the balloon profile data.

8. The method of claim 7, wherein the processor interprets the balloon profile data and displays a multi dimensional image of the ostium based at least partially on the balloon profile data.

9. The method of claim 7, wherein the pump further includes an imaging system that can translate data from at least one imaging modality disposed in the catheter.

10. The method of claim 8, wherein the processor further interprets direct and/or indirect imaging data and the multi-dimensional image of the ostium is based on the direct and/or indirect imaging data.

11. The method of claim 1, further comprising the step of advancing a distal end of a guide device to a desired location in the paranasal sinuses before inserting the catheter, wherein the catheter is inserted into the sinus ostium by advancing the catheter over said guide device.

12. The method of claim 11, further comprising the step of removing the guide device from the paranasal cavity before inflating the balloon.

13. The method of claim 1, wherein the balloon has an outer wall with an abrasive surface such that the repeated deflation and inflation causes the abrasive surface to resect biological material in the sinus ostium.

14. The method of claim 13, wherein the biological material comprises polyps.

15. The method of claim 13, wherein the biological material comprises tumors.

16. The method of claim 13, wherein the biological material comprises edematous tissue.

17. The method of claim 1, further comprising the step of delivering a therapeutic and/or diagnostic agent to the ostium via a delivery lumen of the catheter.

18. The method of claim 17, wherein the step of delivering the therapeutic and/or diagnostic agent to the ostium comprises delivering the agent through at least one opening in the catheter in fluid communication with the delivery lumen.

19. The method of claim 17, wherein the balloon has an outer wall with an abrading surface such that the repeated deflation and inflation causes the abrading surface to abrade biological material in the sinus ostium.

20. The method of claim 19, wherein a wall of the at least one balloon has at least one opening in fluid communication with the delivery lumen, and the step of delivering the therapeutic and/or diagnostic agent to the biological material comprises delivering the agent through said at least one opening and inflating said at least one balloon until it contacts said biological material.

21. The method of claim 17, wherein the therapeutic and/or diagnostic agent comprises an antimicrobial agent.

22. The method of claim 17, wherein the therapeutic and/or diagnostic agent comprises an anti-inflammatory agent.

23. The method of claim 17, wherein the therapeutic and/or diagnostic agent comprises a vasoconstrictor.

24. The method of claim 17, wherein the therapeutic and/or diagnostic agent comprises a mucolytic agent.

25. The method of claim 17, wherein the therapeutic and/or diagnostic agent comprises an anti-histamine.

26. The method of claim 17, wherein the therapeutic and/or diagnostic agent comprises an anti-cholinergic agent.

27. The method of claim 17, wherein the therapeutic and/or diagnostic agent comprises a diuretic.

28. The method of claim 1, wherein the step of inflating the balloon comprises supplying fluid to the balloon with the pump, the pump comprising a hand or foot actuated pump and the balloon diameter is determined by using at least one measurement made by the hand or foot actuated pump.

29. The method of claim 1, wherein the step of inflating the balloon comprises supplying fluid to the balloon with the pump, the pump comprising a pneumo-mechanical pump and the balloon diameter is determined by using at least one measurement made by the pneumo-mechanical pump.

30. The method of claim 1, wherein the step of inflating the balloon comprises supplying fluid to the balloon with the pump, the pump comprising an electro-mechanical pump and the balloon diameter is determined by using at least one measurement made by the electro-mechanical pump.

31. The method of claim 1, wherein the catheter includes at least one imaging marker.

32. The method of claim 1, further comprising the steps of measuring the fluid flow rate as fluid is supplied to the balloon and using the measured fluid flow rate to determine the diameter of the inflated balloon.

\* \* \* \* \*